(12) United States Patent
Vu et al.

(10) Patent No.: US 10,206,888 B2
(45) Date of Patent: *Feb. 19, 2019

(54) CANNABIS-BASED THERAPEUTIC PRODUCT FOR TREATMENT OF CHRONIC PAIN

(71) Applicant: NC3 Systems, San Jose, CA (US)

(72) Inventors: Michael Viet Thang Vu, San Jose, CA (US); Larry Nelson Thacker, Jr., San Juan Capistrano, CA (US); Alex Thacker, San Jose, CA (US); Nelson Miguel Ricardo Martinez, Santa Clara, CA (US); Michael William Bell, Sunnyvale, CA (US)

(73) Assignee: CMG PARTNERS, INC., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/952,875

(22) Filed: Apr. 13, 2018

(65) Prior Publication Data

US 2018/0344663 A1 Dec. 6, 2018

Related U.S. Application Data

(63) Continuation-in-part of application No. 15/616,802, filed on Jun. 7, 2017, and a continuation-in-part of application No. 15/615,829, filed on Jun. 6, 2017.

(60) Provisional application No. 62/638,238, filed on Mar. 4, 2018.

(51) Int. Cl.
| | | |
|---|---|---|
| *A61K 31/05* | (2006.01) | |
| *A61P 43/00* | (2006.01) | |
| *A61K 47/06* | (2006.01) | |
| *B01D 11/02* | (2006.01) | |
| *A61K 9/00* | (2006.01) | |

(52) U.S. Cl.
CPC ............ *A61K 31/05* (2013.01); *A61K 9/0053* (2013.01); *A61K 47/06* (2013.01); *A61P 43/00* (2018.01); *B01D 11/0288* (2013.01)

(58) Field of Classification Search
CPC ....... A61K 31/05; A61K 9/0053; A61K 47/06
See application file for complete search history.

(56) References Cited

U.S. PATENT DOCUMENTS

| | | | |
|---|---|---|---|
| 2005/0266108 A1* | 12/2005 | Flockhart | C07D 311/80 424/774 |
| 2016/0106705 A1* | 4/2016 | Verzura | A61K 31/353 514/454 |
| 2016/0151328 A1 | 6/2016 | Doane et al. | |
| 2016/0250270 A1 | 9/2016 | Wendschuh et al. | |
| 2016/0279073 A1 | 9/2016 | Donsky et al. | |
| 2016/0366926 A1* | 12/2016 | Uren | A24B 3/12 |

* cited by examiner

*Primary Examiner* — Sahar Javanmard
(74) *Attorney, Agent, or Firm* — Galvin Patent Law LLC; Brian R. Galvin

(57) ABSTRACT

A *cannabis* based therapeutic product for treatment of chronic pain produced by separating hash resin from plant material of the *cannabis* plant, pressing the hash resin to expel oil, leaving spent hash resin, extracting further cannabinoids from the spent hash resin using MCT oil, separating the *cannabis* compounds from the oils using high pressure liquid chromatography, flash chromatography, or similar techniques, and processing selected *cannabis* compound formulations into a pill, tablet, liquid, or other form suitable for administration as a therapeutic product for treatment of chronic pain, optionally with the further step of enriching the product with a formulation comprising at least 1% by weight purified -myrcene, prior to processing into a final product.

4 Claims, 2 Drawing Sheets

CANNABIS-BASED THERAPEUTIC PRODUCT FOR TREATMENT OF CHRONIC PAIN

CROSS-REFERENCE TO RELATED APPLICATIONS

This application claims benefit of, and priority to, U.S. provisional patent application 62/638,238, titled "CANNABIS-BASED THERAPEUTIC PRODUCT FOR TREATMENT OF CHRONIC PAIN", filed on Mar. 4, 2018, and is also a continuation-in-part of U.S. patent application Ser. No. 15/616,802, titled "DEVICE FOR DELIVERY OF SMOKABLE CANNABIS AND MANUFACTURING METHOD FOR SAME", filed on Jun. 7, 2017, and is also a continuation-in-part of U.S. patent application Ser. No. 15/615,829, titled "SYSTEM AND METHOD ENHANCED CANNABINOID EFFECT DELIVERY", filed on Jun. 6, 2017, the entire specifications of each of which are incorporated herein by reference.

BACKGROUND OF THE INVENTION

Field of the Invention

The present invention is in the field of *cannabis* active compound formulation for medicinal application. Specifically, the use of formulations containing *cannabis*-derived compounds as medical treatments for chronic pain.

Discussion of the State of the Art

Recently, multiple states have passed legislation legalizing *cannabis* for medical usage. This change promises to greatly increase not only the market for *cannabis*, but also the research into further medicinally important effects of *cannabis* compounds, and the discovery of ways to optimize the effects of known and newly discovered *cannabis* compounds for medical use.

There is a large body of anecdotal evidence that *cannabis*, particularly smoked *cannabis* plant matter, provides substantial relief from chronic pain caused by numerous chronic health conditions such as cancer, multiple sclerosis, arthritis, nerve damage, back pain, fibromyalgia, and similar conditions. These conditions are often resistant to standard treatments, even treatment with opioid medications such as morphine. A substantial body of medical literature supports the anecdotal evidence that *cannabis* compounds can provide relief from chronic pain. However, of the several *cannabis*-based products on the market (ajulemic acid, Cannador®, Marinol®, Cesamet®) that have been studied for their use in treatment of pain, most were developed to treat other symptoms of chronic illness, and most have exhibited modest pain relief, at best. One product, Sativex®, is a *cannabis*-derived oromucosal spray containing equal portions of THC and CBD which has been shown in clinical studies to provide relief from chronic pain. It was approved in Canada in 2005 for treatment of central neuropathic pain in multiple sclerosis, and in 2007 for intractable cancer pain. However, there are many other medical conditions for which *cannabis*-based products may be useful in treating chronic pain.

What is needed is a product that provides these *cannabis* compounds in a form suitable for use as medications and therapies for pain, especially pain caused by chronic conditions such as cancer, multiple sclerosis, arthritis, nerve damage, back pain, fibromyalgia, and similar conditions, and especially where such pain is resistant to standard forms of treatment.

SUMMARY OF THE INVENTION

Accordingly, the inventor has conceived and reduced to practice, in a preferred embodiment, a plurality of formulations for cannabinoid medical and therapeutic benefits. The cannabinoid, terpene, and flavonoid formulations used according to aspects of the invention are intended to mitigate at least one medical issue. For example, the two main cannabinoids in the *cannabis* plant, −9-tetrahydrocannabinol (THC) and cannabidiol (CBD) are known to have analgesic effects by themselves, and may also serve to complement the pain-relieving effects of opioid medications commonly used as a treatment for chronic pain. As another example, the terpene myrcene has analgesic effects, and also increases the permeability of the blood-brain-barrier to other terpenes, cannabinoids, and flavonoids which raises the saturation level of at least one cannabinoid receptor, such as CB1, within the human body. Various formulations of cannabinoids, terpenoids, and flavonoids could be tailored to produce the desired pain-relieving effects for various classes of chronic pain, and may also provide additional benefits such as control of inflammation, which further reduces chronic pain and discomfort.

According to a preferred embodiment, the formulation is compounded into a pill or tablet form, or in a sublingual spray, and is administered orally.

According to another preferred embodiment, the formulation is compounded into a liquid form suitable for inhalation using a vaporizer.

BRIEF DESCRIPTION OF FIGURES

The accompanying drawings illustrate several embodiments and, together with the description, serve to explain the principles of the invention according to the embodiments. It will be appreciated by one skilled in the art that the particular embodiments illustrated in the drawings are merely exemplary, and are not to be considered as limiting of the scope of the invention or the claims herein in any way.

DETAILED DESCRIPTION

Figure 1:
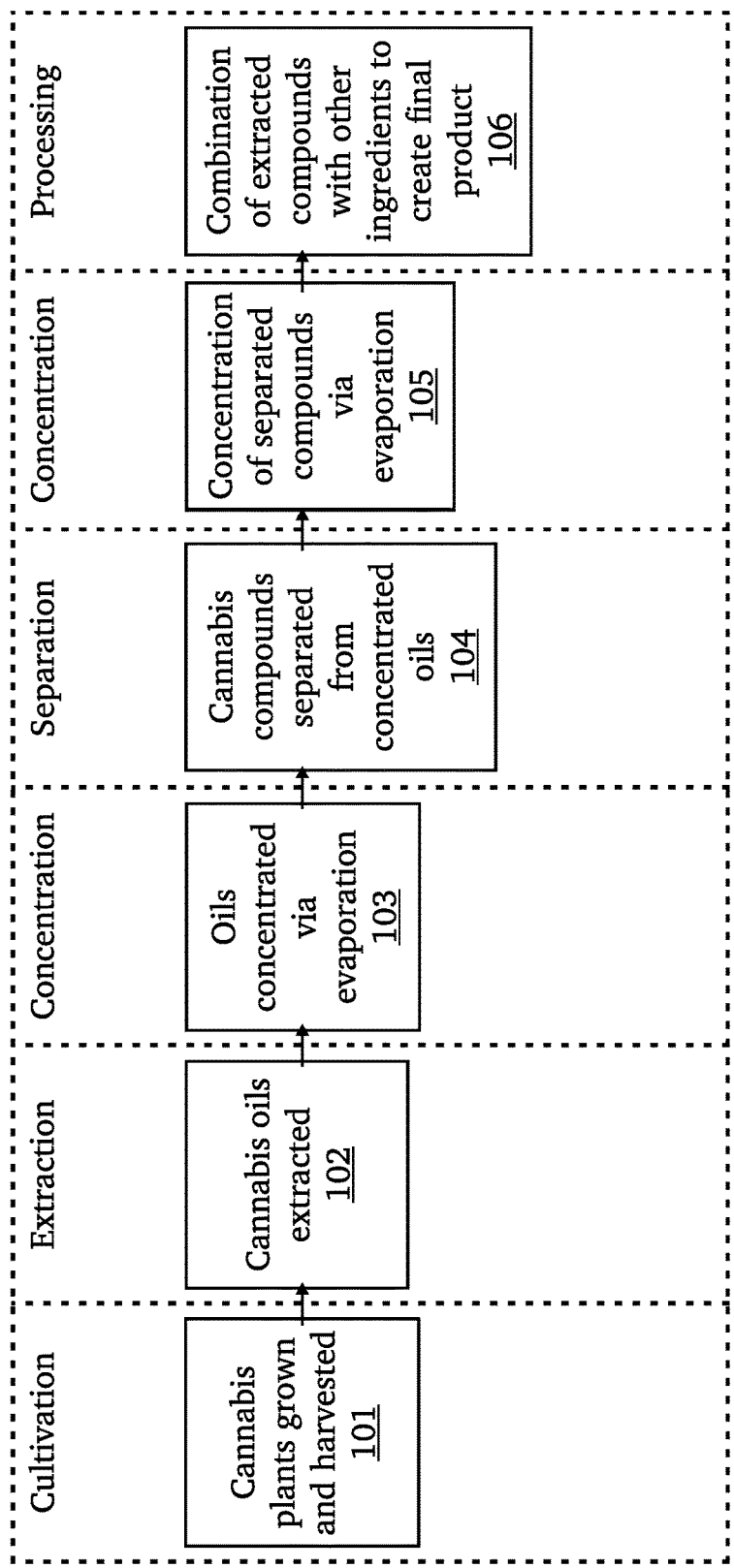
FIG. 1 is a method diagram illustrating a process 100 for preparing *cannabis* medicinal products, according to an embodiment.

Headings of sections provided in this patent application and the title of this patent application are for convenience only, and are not to be taken as limiting the disclosure in any way.

*Cannabis* has been extensively cultivated throughout the world for centuries. Worldwide effects-targeted cultivation has progressed to the point where there are hundreds, if not thousands, of cultivars or strains which contain differing levels of the many active compounds that give *cannabis* its wide range of sought-after medical effects. One family of active compounds that are specific to *cannabis* is the cannabinoid family, of which more than 80 have been identified that may have overlapping but different medical effect profiles. These have been further separated into subclasses comprising: tetrahydrocannabinols (THC); cannabidiols (CBD); cannabichromenes (CBC); cannabinol (CBN); cannabigerols (CBG); cannabinodiol (CBDL); and other cannabinoids (cannabicyclol (CBL), cannabielsoin (CBE), cannabitriol (CBT) and other miscellaneous types.

In raw *cannabis*, the cannabinoids within the flowers' trichomes are carboxylated, meaning they have a COOH carboxylic acid group in their structure. These are mildly, if at all, psychoactive. In order for there to be psychoactivity the cannabinoids must be decarboxylated, or "decarbed" in layman's terms. Non-psychoactive THCA, for example, is decarboxylated to THC, a psychoactive cannabinoid. Both drying (or aging) and heat accomplish this chemical reaction, but the application of heat also results in the loss of certain other *cannabis* components such as the terpenes, which are highly volatile. Both the decarboxylated cannabinoids and the carboxylated cannabinoids exhibit important therapeutic effects for health, and although one can be chemically converted into the other, carboxylated cannabinoids becoming decarboxylated cannabinoids, As used herein both will be referred to as simply cannabinoids.

The biological effects of the cannabinoids may be mediated through two receptors specific for a class of endogenous cell signaling molecules, such as but not limited to N arachidonoylethanolamine also known as AEA or anandamide, a neurotransmitter that predominantly binds to the cannabinoid receptor CB1 and a second compound, 2-arachidonoylglycerol also known as 2-AG which predominantly binds to the CB2 receptor. Expression of the CB1 receptor is found at highest levels in the central nervous system of humans and animals, particularly in the hippocampus, basal ganglia, neocortex, and spine (although expression in peripheral organs such as but not limited to the peripheral nervous system, liver, intestines, and kidneys is also present). Activation of the CB1 receptor has been linked to feelings of euphoria and an increase in appetite, among other effects. Expression of the CB2 receptor is found in the central and peripheral nervous system, the immune system and immune response-related cells, and peripheral organs, among other areas of expression. Activation of the CB2 receptor may have an analgesic effect, reduce inflammation, and increase of immune response towards certain pathogenic bacteria and fungi. The CB2 receptor may also mediate anti-cancer effects attributed to cannabinoids. Most recently, in relation to the CB2 receptor, it has been determined that different ligand agonists may specifically or predominantly activate specific receptor responses indicating a level of ligand functional selectivity for effects linked to the receptor.

Other cannabinoid receptors are found in almost every organ of the body including the skin, the digestive tract, and even in the reproductive organs. Cannabinoid receptors interact with cells in a lock (the cell receptor) and key (the cannabinoid) type of mechanism. The combination of the cell receptors and the cannabinoids comprise the endocannabinoid system, or ECS, which is an intricate network of cell receptor proteins that perform various functions in the body, and is considered to be the greatest neurotransmitter system in the body. Bearing this in mind, it becomes important to realize and understand how *cannabis* can have an impact on numerous health issues including, but not limited to, Alzheimer's disease, memory loss, multiple sclerosis (MS) and other neurodegenerative diseases, and pain control and relief.

The major differences between the various cannabinoids are determined by the extent to which they are psychologically active (psychoactive). Three substantial classes of cannabinoids, including the cannabigerols (CBGs), cannabichromenes (CBCs), and cannabidiols (CBDs), are not known to have psychoactive effects. −9-tetrahydrocannabinol (THC), cannabinol (CBN), and some other cannabinoids are known to be psychoactive to varying degrees. Non-psychoactive CBD is likely the most abundant cannabinoid, contributing up to 40% of *cannabis* resin in some strains (particularly those referred to as hemp strains); CBD has also been implicated in lessening the psychoactive effects of THC.

Of the over 80 known cannabinoid species, those most prevalent and most studied in *cannabis* cultivars are:
THC—9-tetrahydrocannabinol
CBD—cannabidiol
CBC—cannabichromene
CBN—cannabinol
CBG—cannabigerol
THCv—tetrahydrocannabivarin
CBDv—cannabidivarin
−8-THC—−8-tetrahydrocannabinol
THCA—−9-tetrahydrocannabinolic acid
CBDA—cannabidiolic acid A number of these 80-plus cannabinoids display a plurality of important medical effects. The subset of the aforementioned cannabinoids for which these medically beneficial effects are characterized and confirmed are presented here with their chemical formulae and structures.

THC:

As used herein, THC refers to −9-tetrahydrocannabinol, the chemical formula for which is $C_{21}H_{30}O_2$ and the structure of which is:

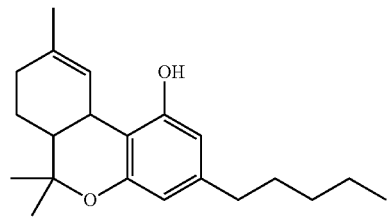 [SMILES: CCCCCc1cc(O)c2c(c1)OC(C)(C)C1CCC(C)=CC21]

THC is recognized as the primary psychoactive compound in *cannabis* and is the most common cannabinoid. Along with its psychoactive properties, THC may be medically used to alleviate several types of pain including the nerve-related pain of diabetic neuropathy and multiple sclerosis. Additionally, THC may be effective in alleviation of the symptoms of PTSD and reduction of nausea and vomiting, particularly that caused by chemotherapy. It has been shown to aid those with anorexia, as well as cancer and HIV associated wasting syndrome as it is an appetite stimulant. It improves breathing for asthmatics, acting as a potent bronchodilator, it relieves eye pressure in patients with glaucoma, improves insomnia, sleep apnea, and reduces nightmares. THC aids those with inflammatory bowel diseases such as Crohn's disease, ulcerative colitis and leaky gut, as well as other intestinal diseases by decreasing intestinal permeability and strengthening intestinal tight junctions. THC slows and prevents Alzheimer's disease and helps control seizures. THC reduces pain and tremors and improves sleep for those with Parkinson's disease. THC, CBD, CBG, and CBC together work synergistically as a powerful cancer tumor-fighting combination. This combination is more powerful than any single one of these working alone.

CBD:

As used herein, CBD stands for cannabidiol, the chemical formula for which is $C_{21}H_{30}O_2$ and the structure of which is:

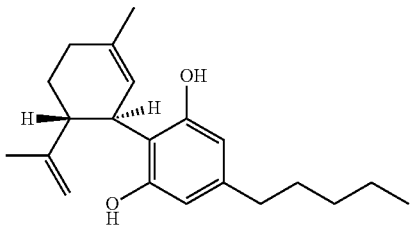 [SMILES: C=C(C)[C@@H]1CCC(C)=C[C@H]1c1c(O)cc(CCCCC)cc1O]

CBD, or cannabidiol, is a non-psychoactive member of the cannabinoids and is one of the most prevalent chemical compounds in the *cannabis* plant. Found predominantly in the resin glands of the female plant, this compound can stop muscle spasms and epileptic seizures, and can reduce idiopathic anxiety, a prevalent and significantly debilitating aspect of mental illness. It is used to treat nicotine addiction, osteoporosis, diabetes, cancer, obsessive-compulsive disorder, Lupus, Parkinson's disease, and motor disorders, and soothes neuropathic and chronic pain. It has anti-inflammatory, antioxidant, neuroprotectant, anxiolytic, antidepressant, analgesic, anti-tumor, and anti-psychotic effects. CBD is powerful all by itself, but it is even more powerful when combined with other cannabinoids such as THC.

CBC:

As used herein, CBC stands for cannabichromene, the chemical formula for which is $C_{21}H_{30}O_2$ and the structure of which is:

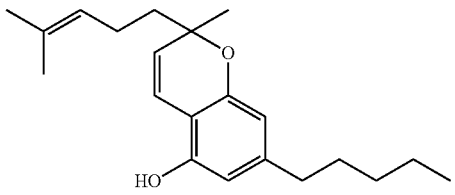 [SMILES: CCCCCc1cc(O)c2c(c1)OC(C)(CCC=C(C)C)C=C2]

Cannabichromene, or CBC, is the third most prevalent cannabinoid in the marijuana plant in general. In some strains CBC is more prevalent than CBD, and like CBD it is non-psychoactive.

CBC is anti-inflammatory and even more so when combined with THC. It has anti-tumor effects and shows promise in fighting breast cancer. When combined with CBD, THC, and CBG, the cancer fighting effects are intensified. It may be useful as an antidepressant and may be more powerful than the other cannabinoids in this capacity. CBC shows antiviral and mild antifungal activity. While CBC addresses several other health issues, including inflammation, cancer, depression, and fungal infections, it also increases the number of brain cells and therefore is useful in the treatment of several brain related disorders. CBC promotes neurogenesis in individuals at any age. This not only affects memory and learning, but can off-set certain dementias which occur when the brain stops growing new cells. It is likely that CBC can alleviate to some extent certain forms of depression and neuro-degenerative diseases via this particular mechanism of neurogenesis.

CBN:

As used herein, CBN stands for cannabinol, the chemical formula for which is $C_{21}H_{26}O_2$ and the structure of which is:

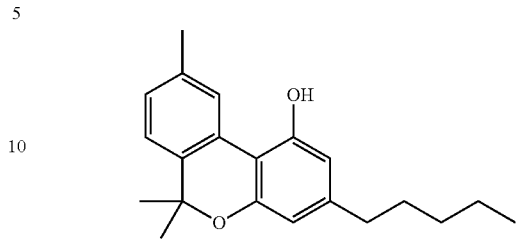

Cannabinol, or CBN, emerges when the dried *cannabis* flower becomes stale; over time, THC and CBD, which are generated by enzymatically-driven synthesis from CBG, break down through oxidative degeneration into CBN. CBN has antibiotic properties, including against methicillin-resistant *Staphylococcus aureus* (MRSA), and also has pain-relieving properties through the release of endorphins. It may delay the onset of, and relieve symptoms of, degenerative motor neural diseases such as amyotrophic lateral sclerosis (ALS) and MS. It works as an appetite stimulant and is more powerful than CBD and CBG in this regard. It has been found to have potent sedative characteristics, making it possibly the most potent single sedative of all the cannabinoids. When combined with THC, CBN has also been found to be effective at lowering the ocular pressure which produces blindness in glaucoma patients. CBN also promises to be useful in future for lowering blood pressure overall.

CBG:

As used herein, CBG stands for cannabigerol, the chemical formula for which is $C_{21}H_{32}O_2$ and the structure of which is:

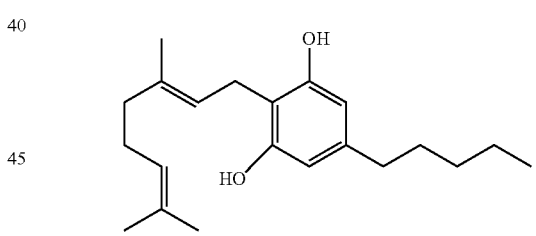

CBG, or cannabigerol, is found in *cannabis* early in the growth cycle, making it somewhat difficult to find in large quantities (CBG is synthesized from smaller constituents, and serves as the feedstock for enzymatic synthesis of THC, CBD, and other cannabinoids, and so CBG is regarded as the source of all cannabinoids. It is non-psychoactive and can also be cultivated in hemp, in which it occurs in greater quantities. CBG has antibiotic properties stronger than CBN and comparable to CBD and is effective against various types of bacteria and fungi. It has therapeutic potential for skin conditions like psoriasis and eczema. CBG is reportedly a more potent pain reliever than THC, and functions as an antidepressant and mood-stabilizer by preventing the uptake of GABA and by increasing serotonin levels in the brain.

THCV:

As used herein, THCV stands for tetrahydrocannabivarin, the chemical formula for which is $C_{19}H_{26}O_2$ and the structure of which is:

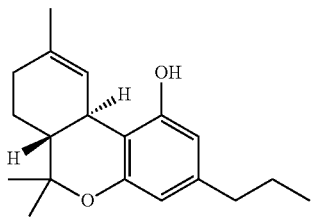 [SMILES: CCCc1cc(O)c2c(c1)OC(C)(C)[C@@H]1CCC(C)=C[C@@H]21]

THCV, or tetrahydrocannabivarin, is one of the several cannabinoids that works in synergy with THC, and mitigates some of the negative psychoactive impacts of THC. THCV's medical uses are antiepileptic, anticonvulsant, and anti-seizure; it is neuroprotective and mitigates some of the short-term memory and speech impairment that comes from THC; it promotes weight loss by suppressing the appetite and possibly decreasing body fat and boosting energy metabolism.

CBDV:

As used herein, CBDV stands for cannabidivarin, the chemical formula for which is $C_{19}H_{26}O_2$ and the structure of which is:

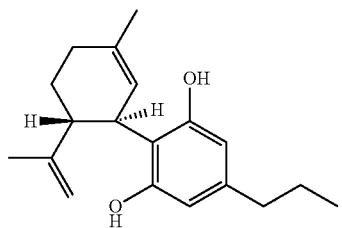 [SMILES: C=C(C)[C@@H]1CCC(C)=C[C@H]1c1c(O)cc(CCC)cc1O]

Cannabidivarin, or CBDV, is a slightly-degraded close relative of CBD. It is used as an anticonvulsant, an antiepileptic, and has antiemetic properties (as well as aiding those with gastrointestinal issues).

−8-THC:

As used herein, −8-THC stands for −8-tetrahydrocannabinol, the chemical formula for which is $C_{21}H_{30}O_2$ and the structure of which is:

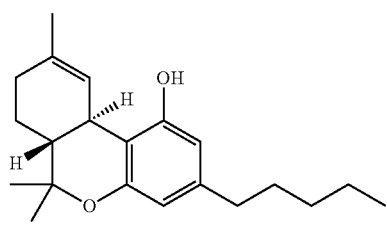 [SMILES: CCCCCc1cc(O)c2c(c1)OC(C)(C)[C@@H]1CCC(C)=C[C@@H]21]

−8-tetrahydrocannabinol is different from −9-tetrahydrocannabinol in that it is less psychoactive. It has both neuroprotective and anti-anxiety properties, as well as being anti-emetic, and may be a stronger appetite stimulant than −9-THC, making it an important consideration for people undergoing chemotherapy.

THCA:

As used herein, THCA stands for −9-tetrahydrocannabinolic acid, the chemical formula for which is $C_{22}H_{30}O_4$ and the structure of which is:

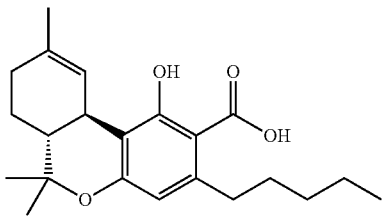 [SMILES: CCCCCc1cc2c(c(O)c1C(=O)O)[C@@H]1C=C(C)CC[C@H]1C(C)(C)O2]

−9-tetrahydrocannabinolic acid, or THCA, is a non-psychoactive compound found in *cannabis* prior to decarboxylation to the psychoactive version, THC, by application of heat or drying or both. THCA levels are particularly high in the live or freshly harvested plant, but as the plant dries, THCA slowly converts to THC, a process expedited by smoking or vaping. Because THCA readily converts to the psychoactive THC upon heat application such as smoking or vaping, it cannot be inhaled or absorbed into the body by these particular means. THCA shows anti-inflammatory properties and may thus be used in treatment of arthritis and lupus. Its neuroprotective properties may make THCA a candidate for treatment of neurodegenerative diseases; its anti-emetic properties making it a possible treatment for nausea and appetite loss, and its anti-proliferative properties making it a candidate in treatment in certain cancers such as but not limited to prostate cancer.

CBDA:

As used herein, CBDA stands for cannabidiolic acid, the chemical formula for which is $C_{22}H_{30}O_4$ and the structure of which is:

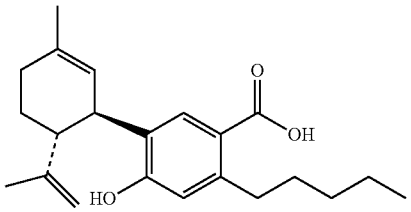 [SMILES: C=C(C)[C@@H]1CCC(C)=C[C@H]1c1cc(C(=O)O)c(CCCCC)cc1O]

Cannabidiolic acid, or CBDA, cannot administered by smoking or vaporizing because doing so decarboxylates it to CBD, similar to THCA conversion to THC. The therapeutic uses for CBDA include antibacterial, anti-emetic, anti-inflammatory, and cancer cell anti-proliferative.

Another family of active compounds present in, but not exclusive to, *cannabis* are the terpenes and decarboxylated terpenes, which are known as terpenoids. Decarboxylation occurs with the removal of the COOH functional group, and can be seen in drawings of the structures. These two terms are commonly used interchangeably, and although they are not chemically identical in structure or chemical formula as terpenoids are decarboxylated versions of some terpenes and exist in plants in this decarboxylated form, for the purposes of this invention both will be referred to as simply terpenes. Though *cannabis* contains up to 200 different terpenes and terpenoids, there are approximately 10 primary terpenes and 20 secondary terpenes that occur naturally in significant concentrations in the *cannabis* plant.

Terpenes are vital components of *cannabis*, and are important medicinally active compounds that are found in up to 1.5% of the total extraction. They are a large and diverse class of organic compounds, produced by a wide variety of plants giving them their flavor, aroma, and color.

Terpenes are the building blocks of a plant's essential oils, and essential oils contain mixtures of the various terpenes found in the plants from which they were extracted.

The isoprene skeleton ($C_5H_8$) may be found in naturally occurring terpenes (also known as isoprenoids), but these terpene compounds do not arise from isoprene itself. Terpenes may be thought of as multiples of isoprene subunits, which is the cornerstone of the "isoprene rule" for terpenes.

The ten primary terpenes and twenty secondary terpenes that occur in significant concentrations are as follows:

The primary terpenes are: myrcene, -pinene, ocimene, terpineol, -caryophyllene, linalool, limonene, terpinolene, valencene, and geraniol.

The secondary terpenes are: phellandrene, carene, terpinene, fenchol, borneol, bisabolol, phytol, camphene, sabinene, camphor, isoborneol, menthol, cedrene, nerolidol, guaiol, isopulegol, geranyl acetate, cymene, eucalyptol, and pulegone.

These terpenes have non-psychoactive therapeutic effects and may be safely used to treat a variety of health conditions. They may also be combined with each other and with cannabinoids, yielding a whole new range of health effects. Some combinations of terpenes act in synergy with boosting effects, while others act as antagonists with effects that inhibit. Some terpenes increase the assimilation of THC, while others may affect the flow of dopamine and serotonin, two of the main regulators of mood and behavior.

Cannabinoid-terpenoid interactions have the potential to produce synergy with respect to the treatment of pain, inflammation, depression, anxiety, addiction, mood and behavior, epilepsy, cancer, fungal infections and bacterial infections, including MRSA.

The primary and secondary terpenes with some of their medical actions are as follows:

Myrcene—Myrcene, specifically -myrcene, is a monoterpene and the most common terpene produced by *cannabis* (some varieties contain up to 60% -myrcene as a fraction of the total terpene content). -myrcene is not found in nature, and was first synthesized in 1965. The chemical formula for -myrcene is $C_{10}H_{16}$ and the structure is:

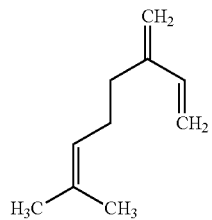

Myrcene is found in most varieties of *cannabis* as well as menthol, lemon grass, and hemp, and is widely used in the perfume industry. Its aroma has been described as musky, earthy, and herbal.

Myrcene has some very special medicinal properties, including lowering the resistance across the blood-brain barrier allowing itself and many other chemicals to cross the barrier more easily and quickly. Myrcene also increases cell membrane permeability, and in the case of cannabinoids like THC, -myrcene allows the cannabinoid to take effect more quickly. More uniquely still, -myrcene has been shown to increase the maximum saturation level of the CB1 receptor, allowing for a greater maximum psychoactive effect.

Myrcene has anti-microbial and anti-septic properties, and acts as a natural anti-depressant, anti-carcinogen and anti-inflammatory agent. It is a potent analgesic, and is anti-mutagenic. It blocks the action of cytochrome, aflatoxin B and other pro-mutagenic carcinogens. It acts as an inhibitor of gastric and duodenal ulcers. Its sedative and relaxing effects make it ideal for the treatment of insomnia and pain.

-Pinene—Alpha-pinene is a monoterpene alkene isolated from pine needle oil as well as from *cannabis*. There are two structural isomers of pinene found in nature: -pinene and -pinene, with -pinene being the most widely encountered terpenoid in nature. With an aroma and flavor of pine, this is partially where pine trees get their scent. The chemical formula is $C_{10}H_{16}$ and the structure is:

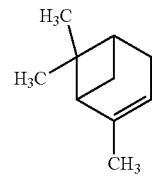

Pinene is one of the principal monoterpenes that is important physiologically in both plants and animals. It tends to react with other chemicals, forming a variety of other terpenes (like limonene), as well as other compounds.

Medicinally, -pinene has an anti-tumor effect and has shown anti-cancer activity. Alpha-pinene is used as an anti-inflammatory, expectorant, bronchodilator, memory enhancer, as a local antiseptic, and it may decrease oil production in oily skin. It acts as a broad spectrum antibiotic and is highly effective against MRSA when combined with the cannabinoids CBD and CBN, all three working in synergy with each other. Alpha-pinene increases alertness and counteracts some of the negative effects of the cannabinoids THC, such as anxiety. It is also believed that the negative memory effects of THC may be lessened if mixed with -pinene.

Ocimene—Ocimene is a group of isomeric monoterpenes found in a wide variety of fruits, spices, and plants. Alpha-ocimene and the two -ocimenes, cis-ocimene and trans-ocimene, differ in the position of the isolated double bond: in the alpha isomer it is terminal. -ocimene exists in two stereoisomeric forms, cis and trans, with respect to the central double bond. Ocimene is often found naturally as a mixture of its various forms. The chemical formula is $C_{10}H_{16}$ and the three structures are:

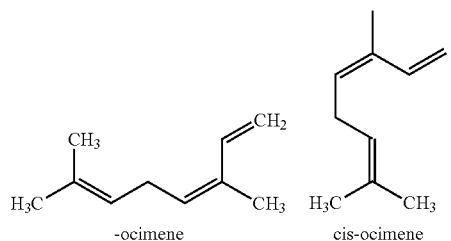

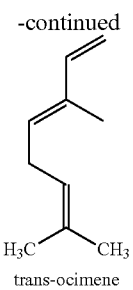
trans-ocimene

Ocimene is recognized by its sweet, fragrant, herbaceous, and woodsy aromas, which feature prominently in several perfumes as well as flavorings, and which help plants defend themselves in their natural environment. Ocimene occurs naturally in botanicals as diverse as *cannabis*, mint, parsley, pepper, basil, mangoes, orchids, kumquats, and allspice.

Ocimene's potential medical benefits include: antiviral, antifungal, antiseptic, decongestant, and antibacterial.

Terpineol—Found in *cannabis* as well as in over 150 other plants, terpineol exists as four isomers: -terpineol, -terpineol, -terpineol and terpinen-4-ol, are four closely related monoterpene alcohols. These are found mixed in plants and their essential oils, with -terpineol comprising the majority of the mixture. The chemical formula is $C_{10}H_{18}O$ and the four structures are:

Terpineol has a floral aroma, resembling lilacs, clove, citrus, or apple blossoms, and other than *cannabis* it also occurs naturally in lilacs, pine trees, lime blossoms, and *eucalyptus*, as well as contributing to the distinctive, pine smoke-based aroma of lapsang souchong tea. From a flavor perspective, terpineol tastes like mint and anise. Terpineol is most frequently found in *cannabis* strains which also contain high levels of -pinene. Due to -pinene's strong aroma, terpineol may be difficult to detect by odor when the two occur simultaneously as the scent of -pinene masks the more delicate floral scent of terpineol.

Terpineol, specifically -terpineol, is known to have calming, relaxing effects and is a mild sedative. Terpineol inhibits skin acne, acts as an antibiotic, anti-inflammatory, antioxidant and has anti-malaria properties. Terpineol's most important property is its anti-cancer property it is able to kill tumors directly.

-Caryophyllene—caryophylene is a bicyclic sesquiterpene with the formula $C_{15}H_{24}$ and the structure:

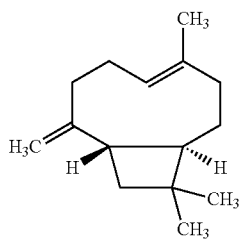

-caryophyllene is found in many plants such as various *cannabis* strains, Thai basil, cloves, cinnamon leaves and black pepper, oregano, and other edible herbs; in minor quantities, it may be found in lavender as well as in many green, leafy vegetables. Its aroma has been described as peppery, woody spicy, and hoppy, as in hops used for brewing beer, to which *cannabis* is closely related.

-caryophyllene is the only terpene known to interact with the endocannabinoid system, and does so at the CB2 receptor, which does not produce a high (that is, the CB-2 receptor is not implicated in *cannabis* psychoactivity). -caryophyllene selectively binds to the CB2 receptor where it is a functional CB2 agonist, giving it an anxiolytic and anti-depressant effect and showing that -caryophyllene may be useful in treating anxiety and depression. -caryophyllene also has anti-oxidant, anti-inflammatory, anti-cancerous, and local anesthetic effects. Further, -caryophyllene is unique for being both a terpene and a dietary cannabinoid, a food component which acts as a cannabinoid and binds to CB2 receptors.

Other phytocannabinoids in combination, especially cannabidiol (CBD) and -caryophyllene, when delivered orally, appear to be promising candidates for the treatment of chronic pain due to their high safety and low adverse effects profiles.

-caryophyllene, through its CB2 receptor-dependent pathway, may be an excellent therapeutic agent to prevent nephrotoxicity (poisonous effect on the kidneys) caused by anti-cancer chemotherapy drugs such as cisplatin.

-caryophyllene has antioxidant and antinociceptive (blocks the sensory neuron detection of pain stimuli) properties. This suggests that high-caryophyllene strains may be useful in treating a number of medical issues such as arthritis and neuropathy pain. It is anti-inflammatory because of its ability to bind directly to the endocannabinoid receptor known as CB2. It is also protective of the cells lining the digestive tract which offers promise for treating some ulcers, and is anti-fungal. -caryophyllene holds promise for cancer treatment.

Linalool—Linalool is a terpene alcohol that occurs as two enantiomers d-linalool and l-linalool, with the chemical formula $C_{10}H_{18}O$ and the structures:

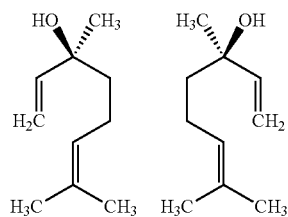

Linalool has a floral lavender aroma with a hint of spice. In addition to *cannabis*, linalool may be found in an array of flowers and spice plants such as lavender, bay laurel, sweet basil, mint, cinnamon, citrus and even some fungi. Linalool is a critical precursor in the formation of vitamin E.

Linalool may be used as an anti-inflammatory or as an immune booster, and may significantly reduce lung inflammation caused by cigarette smoke as well as reducing lung irritation potentially caused by inhaling *cannabis* smoke. Linalool helps to restore cognitive and emotional function partially via its anti-inflammatory effect, and may therefore be used to treat various forms of dementia, and particularly Alzheimer's disease. It helps with insomnia, and because it also lessens the anxiety brought on by pure THC, it helps in the treatment of anxiety and psychosis. Linalool has anesthetic effects and is calming, relaxing and mood lifting, and helps reduce headaches and migraines. Linalool may be useful to help treat liver cancer, and also helps to modulate motor movements, giving it anti-epileptic properties. It is an effective insecticide against fruit flies, fleas, and cockroaches, making it useful as an insect repellant and for use in and around the home and garden.

Limonene—Limonene is a monocyclic monoterpene and one of two major compounds formed from pinene. It exists as two enantiomers, d-limonene and l-limonene, and has the chemical formula $C_{10}H_{16}$. The structures are:

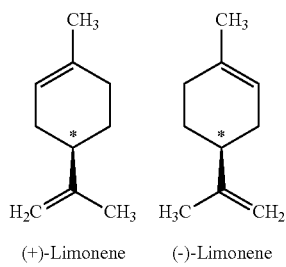

(+)-Limonene    (-)-Limonene

Limonene has a citrusy aroma and the more common d-isomer smells like oranges. While it is found in *cannabis*, it is also present in citrus fruit and especially lemons, juniper, and peppermint. It assists in the absorption of other terpenes through the skin and other body tissues. Limonene has anti-fungal, anti-bacterial, and anti-depressant effects; it promotes a general uplift in mood and attitude, and it helps promote weight-loss. It is a strong antioxidant and exerts anti-carcinogen properties as it may reduce the formation of some tumor growths and alleviate fat buildup in the liver induced by diet. Limonene is known to increase blood pressure which is useful for those with low blood pressure. It has very low toxicity and adverse effects are rarely associated with it.

Terpinolene—Terpinolene, also called -terpinene (-terpinene), is one of a class of isomeric monoterpenes, all of which have the chemical formula $C_{10}H_{16}$, and which differ from each other only in the position of the carbon-carbon double bonds. The -terpinene, -terpinene, -terpinene (terpinolene) are all found in plant essential oils, whereas -terpinene is synthetically prepared from sabinene. The chemical structures are:

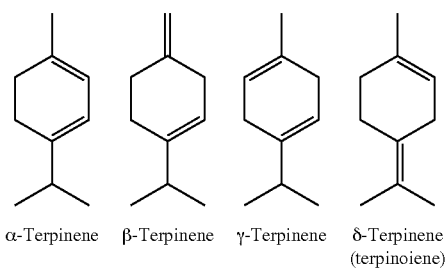

α-Terpinene    β-Terpinene    γ-Terpinene    δ-Terpinene
                                              (terpinoiene)

Terpinolene is characterized by a fresh, piney, floral, herbal, sometimes smoky or woody, and occasionally citrusy aroma and flavor. It is found in a variety of fragrant plants including *cannabis*, nutmeg, tea tree, conifers, citrus, apples, cumin, marjoram, sage, rosemary, Monterey cypress, and lilacs. It is used in soaps, perfumes, cosmetics, flavorings, and in the semiconductor industries.

Terpinolene is a central nervous system depressant used to induce drowsiness or sleep or to reduce psychological excitement. It has a sedative effect when inhaled, making it useful for insomnia and anxiety.

Terpinolene markedly reduces the expression of the AKT1 gene, which produces the protein AKT1 kinase, an enzyme that plays a vital role in various important signaling pathways and cellular processes. AKT1 kinase helps regulate cell growth and division (proliferation), differentiation, cell survival, and apoptosis (cell death) when cells become damaged or are no longer needed. The AKT1 gene belongs to the class of genes known as oncogenes. When mutated, oncogenes have the potential to cause normal cells to become cancerous. The activation of AKT is connected with many types of cancers as it increases cell proliferation and suppresses apoptosis. By suppressing the AKT1 gene expression, both rampant cell proliferation and lack of apoptosis are suppressed, making terpinolene a valuable anti-cancer agent.

Terpinolene, together with vitamins A and E, prevents the oxidation of "bad cholesterol" (low-density lipoprotein, or LDL) and is therefore helpful in the treatment of heart disease.

Terpinolene's potential medical benefits include: antioxidant, sedative, antibacterial, antifungal, insect repellent, anti-proliferative (anti-cancer) and non-genotoxic, making it very safe and very healing.

Valencene-Valencene is a bicyclic sesquiterpene with chemical formula $C_{15}H_{24}$ and is found in Valencia oranges as well as *cannabis* The chemical structure is:

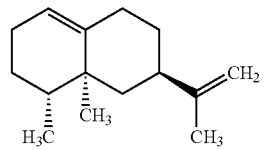

It has a sweet, fresh, citrusy, woody, aroma and flavor and is used in both the flavor and perfume industries.

Valencene is toxic to ticks and mosquitoes at lesser concentrations than DEET and doesn't have the toxicity of DEET. Valencene is an effective insect repellent for ticks, mosquitos, and other insects. It is also anti-inflammatory, and may lower the levels of inflammatory markers in macrophages.

Geraniol-Geraniol is an acyclic monoterpene alcohol whose formula is $C_{10}H_{18}O$ and which boils at about 447° F. and frequently occurs in strains that also produce linalool. Not only from *cannabis*, geraniol is also found in rose, geranium, lime, lemon, lemongrass, nutmeg, bergamot, carrot, coriander, lavender, blueberry, blackberry, and tobacco. Geraniol emits a rose-like scent that makes it a popular perfume additive. The chemical formula is:

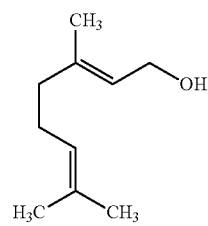

Geraniol is an effective mosquito repellent, an antioxidant, and shows a potential protective effect against neuropathy. It is anti-cancer and inhibits the growth and biosynthesis of colon cancer cells, and when combined with farnesol and perill alcohol, suppress pancreatic tumor growth making it especially useful for cancer of the pancreas which currently is extremely difficult to cure.

Secondary Terpenes:

Phellandrene—Phellandrene refers to a pair of cyclic monoterpenes that have a similar molecular structure and similar chemical properties, -phellandrene and -phellandrene, which are double-bond isomers of each other. In -phellandrene, both double bonds are endocyclic (within the ring structure) and in -phellandrene, one of them is exocyclic (external to the ring structure). Phellandrene has the chemical formula $C_{10}H_{16}$ and is described as pleasant, fresh, citrusy, minty and peppery-woody. The chemical structures are:

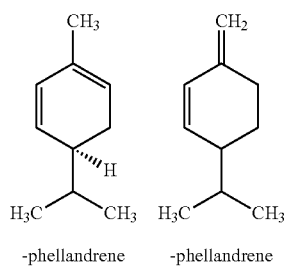

-phellandrene    -phellandrene

Phellandrenes are used in the perfume and the flavoring industries because of their pleasing aromas and because they are absorbed through the skin. -phellandrene may form dangerous, explosive peroxides on contact with air at elevated temperatures. -phellandrene is non-hazardous, and both phellandrenes may be found in *cannabis* as well as in spices such as allspice, cinnamon, garlic, dill, pepper, parsley, and in the essential oils of *angelica, eucalyptus, lavandula, mentha, fennel, ginger*, and *Pinus* species.

Insoluble in water but miscible with ether, phellandrene is one of the easiest terpenes to identify in the lab. When a solution of phellandrene in a solvent (or an oil containing phellandrene) is treated with a concentrated solution of sodium nitrate and then with a few drops of glacial acetic acid, very large crystals of phellandrene nitrate speedily form.

Phellandrene has special medicinal values and has been used in traditional Chinese medicine to treat digestive disorders. It is one of the main compounds in turmeric leaf oil, which is used to prevent and treat systemic fungal infections. Phellandrene possesses antidepressant properties and is also used as an insecticide.

Carene—3-Carene is a bicyclic monoterpene with a sweet, pungent odor. It is found naturally in *cannabis* and in many healthy, beneficial essential oils, including cypress oil, juniper berry oil and fir needle essential oils, and is a main constituent of pine and cedar resin. It is also present in bell pepper, basil oil, grapefruit and orange juices, citrus peel oils from fruits like lemons, limes, mandarins, tangerines, oranges, kumquats, and it is a major component of turpentine, comprising as high as 42% depending on the source. The chemical formula is $C_{10}H_{16}$ and the chemical structure is:

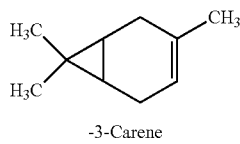

-3-Carene

-3-Carene is used as a flavoring in many products.

It is nontoxic, but may cause irritation when inhaled. It is possible that high concentrations of -3-carene in some strains may be partly responsible for symptoms of coughing, itchy throat, and eye afflictions when smoking *cannabis*

-3-carene is an effective anti-inflammatory. In higher than natural concentrations, -3-carene may be a central nervous system depressant and a skin irritant. It is often used to dry out excess body fluids, such as tears, runny noses, sweat, and menstrual flows.

Terpinene—Terpinenes are a group of isomeric terpenes with the chemical formula $C_{10}H_{16}$ and this group is composed of three natural isomeric terpenes and one synthetic one that differ from each other in the positions of the carbon to carbon double bond. -terpinene, -terpinene (terpinolene), and -terpinene are naturally occurring, whereas -terpinene is not found in nature but may be synthetically produced from sabinene. -terpinene is also called terpinolene. The chemical structures are:

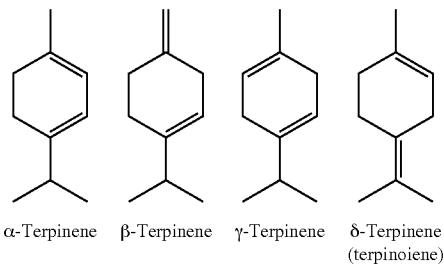

α-Terpinene    β-Terpinene    γ-Terpinene    δ-Terpinene
(terpinoiene)

Terpinene is a major component of essential oils made from citrus fruits, and has a lemon odor. -terpinene is widely used in the flavor, perfume, cosmetics, soap, pharmaceutical industries, as well as in food and confectionary.

Terpinene is considered to be a well-tolerated additive in the pharmaceutical industry, and it has very strong antioxidant properties.

Fenchol-Fenchol, also called 1,3,3-trimethyl-2-norbornanol, is a terpene and an isomer of borneol with the chemical formula $C_{10}H_{18}O$ and the chemical formula is:

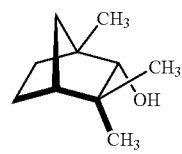

This particular terpene is an enantiomer, d-fenchol or (1R)-endo-(+)-fenchol, but it has no mirror image found in nature, thus it is enantiopure.

Found in *cannabis*, it also occurs naturally in basil, fennel, nutmeg, pine, rosemary oil, lime oil, beer and more. It has a bitter, lime flavor and is used extensively in perfumes, flavorings, soaps, detergents, and personal care products. It is known to exhibit antibacterial properties.

Borneol—Borneol, a terpene alcohol, has the chemical formula $C_{10}H_{18}O$ and exists naturally as two enantiomers, l-borneol and d-borneol, both of which are found in nature. It is easily oxidized to camphor, has an aroma of camphor, mint, and earth, and is a component of many natural essential oils. It is found in *cannabis* resin and herbs like thyme, rosemary, and cinnamon. The chemical structure is:

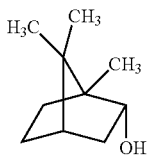

Borneol is used in the perfume industry, as well as in dietary and herbal supplements in the USA.

Borneol is used as a calming sedative, it is used to fight fatigue, stress, to relax, and to recover from illness. Borneol is used as an anti-inflammatory, an anti-nociceptive/analgesic, a skin tonic, a local anesthetic, as an anti-insomnia, anti-septic, a digestive aid, a sedative and an antispasmodic. It is used to improve circulation, to reduce pain and swelling, as a bronchodilator, a cough suppressant, and an insect repellant.

Bisabolol—Also called levomenol, -bisabolol is a natural monocyclic unsaturated sesquiterpene alcohol with the chemical formula $C_{15}H_{26}O$ and a chemical structure of:

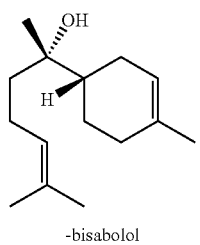 [SMILES: CC(C)=CCC[C@](C)(O)[C@@H]1CC=C(C)CC1]

-bisabolol

-bisabolol is found in cannabis, the Brazilian shrub candeia, and German chamomile. It has a floral aroma.

-bisabolol, which is nontoxic and nonirritating to the skin, possesses anti-inflammatory and wound healing properties, as well as antimycotic and antibacterial effects, and may be used as a deodorizer. It is a potent inhibitor of fungi, Candida albicans, and gram-positive bacteria. It shows promise in the treatment of certain cancers as it induces apoptosis in leukemia.

Phytol—Phytol is a natural linear diterpene alcohol with the chemical formula $C_{20}H_{40}O$ that may be used as a precursor to prepare synthetic forms of vitamin E and vitamin K1. Found in cannabis and green tea, phytol results from the degradation of chlorophyll and is an oily liquid that is nearly insoluble in water, but soluble in most organic solvents. The chemical structure is:

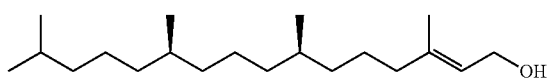 [SMILES: C/C(=C\CO)CCC[C@H](C)CCC[C@H](C)CCCC(C)C]

Phytol inhibits the enzyme that degrades the neurotransmitter GABA (-aminobutyric acid), which may partially account for its relaxing effect. In the body, phytol is essential in activating enzymes that have a positive effect on the production of insulin. It is beneficial in regulating blood glucose, for reducing blood pressure and for reducing cholesterol levels in blood.

Camphene—Camphene is a bicyclic monoterpene with the chemical formula $C_{10}H_{16}$ and the chemical structure:

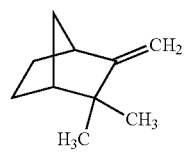

Camphene readily volatilizes at room temperature and has a pungent odor similar to camphor. It is a minor component of many essential oils such as turpentine, cypress, neroli, valerian camphor, citronella and ginger. It is used as a flavoring for food, and in the perfume industry. It is produced industrially by catalytic isomerization of the more common -pinene.

Camphene is found in essential oils extracted from cannabis and certain trees, and it may play a critical role in cardiovascular health. Camphene possesses antioxidant, anti-inflammatory, and antibiotic characteristics, and shows promise for pain relief.

Camphene may reduce plasma cholesterol and triglycerides. Given the importance this plays in heart disease, camphene might be used as an alternative to pharmaceutical drugs which cause intestinal problems, liver damage, and muscle inflammation.

Sabinene—Sabinene is a bicyclic monoterpene with the chemical formula CH, and exists as d and l enantiomers. The chemical structures are:

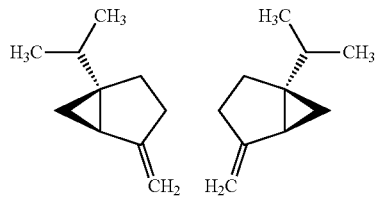

d Sabinene    l Sabinene

It has an aroma of spice, pine, and orange, and is found in many plants including cannabis, Norway spruce, black pepper, basil, and Myristica fragrans the world's main source of nutmeg. It is used in the perfume industry and in the food industry as a flavoring.

Sabinene has antioxidant and anti-inflammatory properties, and benefits liver function, digestion, relieves arthritis, and may soothe skin conditions.

Camphor—Camphor is a waxy, flammable, white crystalline solid with the chemical formula CHO. Camphor occurs naturally as d-camphor, the l-enantiomer being synthetically produced.

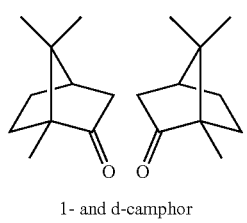

l- and d-camphor

It is commonly found in cannabis, rosemary leaves, camphor basil, and in Cinnamomum camphora, which goes by several common names including camphor tree, camphorwood, and camphor laurel. Camphor is also found in kapur trees, and a few other related trees in the laurel family, notably *Ocotea usambaensis*.

The ancient Egyptians used camphor as one of the ingredients used for mummification. It has been used as an ingredient in sweet and savory foods in medieval Europe and Arabia. Camphor is readily absorbed through the skin, and when applied topically produces a cooling sensation similar to that of menthol. It acts as a slight local anesthetic, relieves pain, itching and swelling, and has antimicrobial properties. It is used as a cough suppressant, a decongestant, an insect repellant notably for cockroaches and fleas, and is used to make mothballs. Camphor has been used to treat sprains, swellings, inflammation, and fevers. In very small quantities taken internally, it is used to treat minor heart symptoms and fatigue. Camphor increases heart rate, is a skin vasodilator, and reduces appetite.

Isoborneol—Isoborneol is a bicyclic terpene alcohol with the chemical formula $C_{10}H_{18}O$ and the chemical structure:

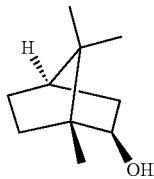

Isoborneol is a waxy solid with an odor similar to that of camphor, and is found in *cannabis* and mugwort. Isoborneol exhibits antiviral properties and is a potent inhibitor of herpes simplex virus type 1. Besides being antiviral, it also has antioxidant, anti-inflammatory, and antimicrobial properties.

Menthol—Menthol is a terpene alcohol with the chemical formula $C_{10}H_{20}O$ and the chemical structure:

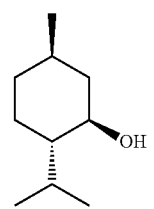

Menthol is found in *cannabis* and in members of the mint family such as corn mint and peppermint. Menthol is a white or colorless crystalline solid at room temperature. It is used in candies, cigarettes, cosmetics, personal care products, and medicines.

Menthol produces a cooling sensation on the skin and soft tissues of the mouth by activating the TRPM8 receptor protein that senses the change in temperature in cold-sensing nerves. However, menthol gives a cool sensation without any actual fall in temperature in that area. This lowers inflammation in the area, causing the nearby blood vessels to dilate, and increases blood flow to the area which delivers fresh nutrients to repair the area and removes any toxic wastes generated. This process speeds healing. Menthol may also bind to another receptor called kappa opioid receptor that may also produce a numbing effect.

Menthol exhibits analgesic properties and is used topically to treat inflammatory pain caused by conditions such as arthritis, bursitis, tendonitis, muscle strains or sprains, backache, bone pain, bruising, and cramping.

Menthol cigarettes have a lower cancer risk and cause far less cigarette related cancers than their non-mentholated counterparts, making menthol an important and possibly mitigating component of inhaled *cannabis*.

Cedrene—Cedrene is a sesquiterpene with the chemical formula $C_{15}H_{24}$ and exists in two isomeric forms, -cedrene and -cedrene, which differ in the position of one double bond.

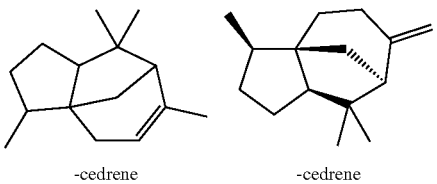

-cedrene                -cedrene

Cedrene is a light yellowish transparent oil with the aroma of cedar wood and is found in *cannabis*, fenugreek, and in the essential oil of cedar.

Cedrene possesses antiseptic, antimicrobial, antifungal, and anticancer properties, particularly against T-cell lymphoma, which may occur in the blood as leukemia or in lymph nodes (lymphoma), skin, or other areas of the body.

Nerolidol—Also known as peruviol, nerolidol is a naturally occurring sesquiterpene alcohol present in various plants with a floral odor, and has the chemical formula $C_{15}H_{26}O$. It exists in two isomeric forms, cis and trans, which differ in their geometry about the central double bond. The chemical structures are:

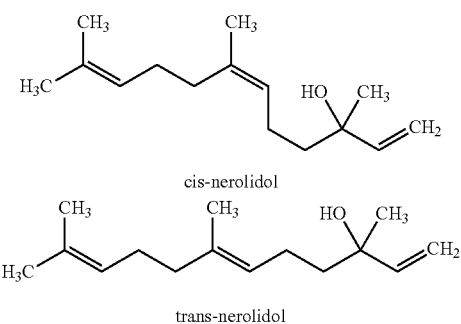

cis-nerolidol trans-nerolidol

Nerolidol has a floral, citrus, woody, fresh bark aroma, and may be found in *Cannabis sativa*, neroli, niaouli, ginger, jasmine, lavender, tea tree, citronella, lemon grass, and *Brassavola nodosa*, a Mexican orchid.

Nerolidol is widely used in perfumes as both a base note fragrance component and as a fixative; it is also used in cosmetics, personal care products, detergents and cleaning products, and as a food flavoring agent.

It has anti-fungal, anti-leishmaniasis (an infection caused by protozoan *Leishmania* parasites, which are spread by the bite of phlebotomine sand flies) and anti-malarial properties. It also produces a sedative effect. It may enhance skin penetration for the transdermal delivery of therapeutic drugs.

Guaiol—Guaiol, also called champacol, is a sesquiterpenoid alcohol found in several plants, including *Cannabis indica*, guaiacum and cypress pine. It is a crystalline solid at room temperature with the chemical formula $C_{15}H_{26}O$ and the structure:

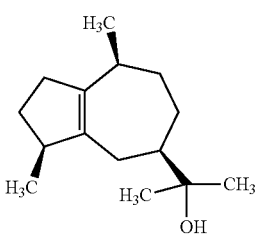 [SMILES: C[C@H]1CC[C@@H](C(C)(C)O)CC2=C1CC[C@@H]2C]

Guaiol has a woody, rosy, floral aroma. *Cannabis* strains known to contain guaiol include Liberty Haze, Blue Kush, Chocolope, and Medical Mass.

Guaiol has been used for centuries as a treatment for diverse ailments ranging from coughs to constipation to arthritis and syphilis. It is also an effective insect repellent and insecticide. Guaiol's potential medical properties include: Antimicrobial, Anti-inflammatory, laxative, diuretic, and insect repellant.

Isopulegol—Isopulegol is a monoterpene alcohol found in *cannabis*, corn mint, European pennyroyal, lemongrass and geranium, and possesses a minty aroma. It has the chemical formula $C_{10}H_{18}O$ and the structure:

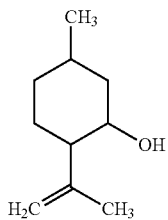

Isopulegol is used as a flavoring agent in food, in cosmetics, and in perfumes, personal care products, and cleaners. It is a chemical precursor to menthol, and shows many promising routes for therapeutic use. Isopulegol possesses gastroprotective, anti-convulsive, anti-inflammatory, antioxidant, and stress-reducing effects, and it reduces the severity of seizures and anxiety in animal models.

Geranyl Acetate—Geranyl acetate has several other names including geraniol acetate, and is a monoterpene ester with a sweet, strong, floral rose and fruity aroma. It is a colorless liquid at room temperature and has the chemical formula $C_{12}H_{20}O_2$ with the structure:

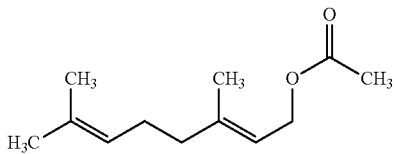

It is used in the fragrance and flavor industries, and is found in products such as soaps, detergents, personal care products, fabric softeners, and as a middle note in perfumes.

Geranyl acetate is found in a variety of natural essential oils, such as *cannabis*, citronella, palmarosa, geranium, coriander, neroli, lemongrass, petitgrain, carrot, *sassafras*, rose, and many others. It exhibits strong antimicrobial, antifungal, and anti-inflammatory effects.

Cymene—Also called p-cymene, para-cymene, methyl-isopropyl-benzene, and 1-isopropyl-4-methylbenzene among others, this aromatic, para substituted benzene ring is an alkylbenzene monoterpene with the formula $C_{10}H_{14}$ and the structure:

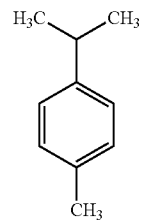

The other two isomers of methyl-isopropyl-benzene are o-cymene (orthocymene) and m-cymene (meta cymene), however only p-cymene is a naturally occurring compound. It has a citrusy-woody-spicy odor with herbal hints, and is found in cumin, thyme, anise, coriander, mace, oregano, *eucalyptus* and in *angelica* root and *angelica* seed oil, bay leaf oil, basil oil, carrot seed oil, clove bud oil, clary sage oil, and grape fruit oil. It is used in flavoring beverages, cakes and confectionery, as well as in the fragrance, paint, and furniture industries.

P-cymene has documented anti-inflammatory effects, it shows potential protective effects against acute lung injury, and is effective against pathogenic bacteria, especially *Escherichia coli*. When combined with carvacrol it is also antibacterial and possibly even more so. P-carvacrol, thymol and p-cymene work synergistically together and have antifungal properties; p-cymene by itself showed strong antifungal activity against numerous *candida* species. P-cymene also shows anti-inflammatory, antinociceptive and analgesic properties.

Eucalyptol—Eucalyptol has many other names, including 1,8-cineol, cajeputol; 1,8-epoxy-p-menthane, and eucalyptole. Eucalyptol is a cyclic monoterpenoid ether and it is the main component of *eucalyptus* essential oil having the chemical formula $C_{10}H_{18}O$ and the chemical structure:

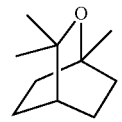

Eucalyptol has a minty, earthy, spicy aroma and is found in several plants including *Cannabis sativa*, camphor laurel, bay leaves, tea tree, mugwort, sweet basil, wormwood, rosemary, common sage, and other aromatic plants. Eucalyptol is used in flavorings in baked goods, confectionery, meat products, beverages, and mouth wash; in fragrances, cigarettes and cosmetics.

Eucalyptol has many medicinal uses, it relieves pain, suppresses coughs, and improves concentration and inner balance. Plants containing eucalyptol enhance meditation and concentration. Eucalyptol has potent antifungal effects and is used as an insecticide and insect repellent. Eucalyptol inhibits cytokine production in lymphocytes and monocytes, giving it an anti-inflammatory effect, and it reduces inflammation and pain when applied topically. It is able to kill in vitro leukemia cells of two cultured leukemia cell lines. Eucalyptol is effective for controlling asthma and reduces airway mucus hypersecretion by its anti-inflammatory cytokine inhibition, and it is an effective treatment for nonpurulent rhinosinusitis.

Pulegone—Pulegone, a monocyclic monoterpenoid, is a secondary terpene component of *cannabis*. It exists naturally in two enantiomeric forms, d-pulegone and l-pulegone, with d-pulegone being the most abundant. The chemical formula is $C_{10}H_{16}O$ and the structure is:

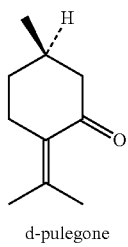

d-pulegone

It has an aroma of peppermint and camphor, and it is found in several plants besides *cannabis*, such as catnip, peppermint, spearmint, pennyroyal, and rosemary. It is used for flavoring foods, drinks, and dental products, as a spice, it is used as fragrance components in detergents and cosmetics, it is used in herbal medicines, perfumery, and aromatherapy.

Pulegone is an emmenagogue, a mucolytic, and is good for congestion of the respiratory system. Pulegone may have significant sedative and fever-reducing properties. It may also alleviate the side effects of short-term memory loss sometimes associated with higher levels of THC. Pulegone is a powerful insecticide.

Traditionally, plants containing pulegone, such as pennyroyal, have been used as herbal teas for non-ulcer dyspepsia, primary dysmenorrhoea, secondary amenorrhoea and oligomenorrhoea, as an abortifacient, and as a diaphoretic. Pennyroyal essential oil has been used for the same conditions. Pulegone is a hepatotoxic (liver poison) and nephrotoxic (kidney poison) constituent of the folklore abortifacient pennyroyal oil.

Today, *Mentha piperita* (peppermint) and *Mentha pulegium* (pennyroyal) are used for colds, headache, migraine, as a diuretic, antispasmodic, anticonvulsive, anti-emetic, heart stimulant, sedative, and to treat the symptoms of inflammatory bowel syndrome. Rosemary inhibits acetylcholinesterase in the brain yielding more acetylcholine and allowing nerve cells to communicate more effectively with one another, giving promise for treatment of memory issues and dementias.

One other terpene found in *cannabis* that bears mentioning is humulene.

Humulene—Humulene is a monocyclic sesquiterpene containing an 11-membered ring and is also known as -humulene and -caryophyllene (an isomer of -caryophyllene). Humulene is often found in combination with it's isomer, -caryophyllene, it has the chemical formula $C_{15}H_{24}$ and the structure is:

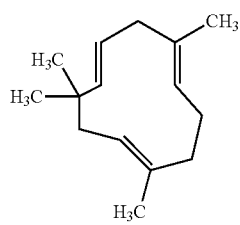

Humulene is found in *Cannabis sativa* strains, hops and Vietnamese coriander, pine trees, orange trees, marsh elders, tobacco, sage, *ginseng*, ginger, and sunflowers, among other plants. Humulene is what gives beer its distinct "hoppy" aroma, and also contributes to the same hoppy aroma in *cannabis*.

Humulene is anti-tumor, anti-bacterial, is a strong anti-inflammatory, and is anorectic (suppresses appetite). It is often blended with -caryophyllene and used as a potent remedy for inflammation. Humulene aids in weight loss by acting as an appetite suppressant.

In the body, terpenes act on receptors and neurotransmitters. They readily combine with, or dissolve in, lipids or fats. Terpenes may act as serotonin uptake inhibitors, they may enhance norepinephrine activity, they may increase dopamine activity, and they may augment synaptic -aminobutyric acid (GABA) levels by inhibiting re-uptake. These actions are similar to many of the commonly prescribed anti-depressant drugs used today The differences in the amounts and types of both cannabinoids and terpenes, along with the other lesser compounds within the *cannabis* varieties, imbue the various *cannabis* extracts with medicinal significance. Adding or increasing one or more of these compounds can alter the effects of *cannabis* extract, as certain compounds work in synergy to augment desirable effects while other compounds act as antagonists to inhibit undesirable effects.

*Cannabis* has been used to treat pain since at least the third millennium BC. In recent decades, and especially since changes in state laws allowing medical use of *cannabis*, there has developed a substantial body of anecdotal evidence that *cannabis*, particularly smoked *cannabis* plant matter, provides substantial relief from chronic pain caused by numerous chronic health conditions such as cancer, multiple sclerosis, arthritis, nerve damage, back pain, fibromyalgia, and similar conditions. In fact, smoked *cannabis* plant matter appears to be a preferred method of pain treatment by those with chronic medical conditions, even though other forms of administration of *cannabis* are available for medical use. This preference is likely due to a variety of factors. First, smoking *cannabis* allows the user to easily control the dosage, as the effects are felt quickly, and additional amounts can be smoked if the initial effects are insufficient. Second, the concentrations of active *cannabis* compounds in the bloodstream are high compared to oral administration, and more powerful, as the active *cannabis* compounds go directly into the bloodstream instead of being processed into other compounds by the liver. Third, the combined effect of the dozens of *cannabis* compounds in *cannabis* plant matter may provide a more pleasant subjective effect, or other benefits such as reduced inflammation, beyond that of a purified cannabinoid medical product. In an aspect of the embodiment, *cannabis* compounds can be selected in formulations designed to specifically to address each of these issues, while avoiding the detriments of smoked *cannabis* plant matter, such as respiratory irritation and the increased potential for lung disease. Further arguing in favor of specifically-formulated *cannabis*-based products is the fact that certain modern North American and European strains of *cannabis* display relatively high concentrations of THC (a potent psychoactive compound), but relatively little CBD or other phytocannabinoid content.

A substantial body of medical literature supports the anecdotal evidence that *cannabis* can be used to treat chronic pain. The endocannabinoid system is active in the control of pain. Compounds found in *cannabis* act on the endocannabinoid system, and certain of these compounds have a powerful analgesic effect. For example, THC is believed to be ten times more powerful than morphine in mediating pain in wide dynamic range neurons in the ventroposterolateral nucleus of the thalamus. Cannabidiol (CBD) is also believed to have strong analgesic effects, due to its function as an endocannabinoid modulator, likely through its ability to promote signaling of the adenosine receptor A2A by inhibiting the adenosine transporter. Cannabigerol (CBG), a "minor cannabinoid" found in small quantities in *cannabis*, is believed to have even greater analgesic activity than THC.

Chronic pain conditions are often resistant to standard treatments, including treatment with opioid medications such as morphine. There is some medical evidence that suggests that cannabinoids are complementary to treatment with opioids, offering additional pain reduction on top of that provided by the opioids. Combining *cannabis* treatments for chronic pain with opioid treatments for chronic pain may have the benefit of reducing patient pain levels, reducing reliance on (and addiction to) opioids, or both.

The inventor has conceived, and reduced to practice, a variety of *cannabis* formulations for the treatment of chronic pain. In one exemplary aspect of the embodiment, different combinations of THC, CBD, and CBG may be used to obtain the desired amount of pain relief due to chronic illnesses. In another exemplary aspect of the embodiment, different combinations of THC, CBD, and CBG may be used to complement and enhance opioid pain treatments, and to manage pain while reducing dependence on opioids.

The inventor has also conceived, and reduced to practice, a variety of *cannabis* formulations for the delivery of an enhanced cannabinoid effect employing the terpene myrcene. This not only raises the saturation level of a predominant cannabinoid receptor such as CB1 for cannabinoids such as THC, but also increases permeability of the cell membrane and decreases the resistance across the blood-brain barrier for medicinal compounds known to be present in *cannabis* extracts, thus potentiating the effects of these medically effective compounds at several major sites of action.

In one exemplary aspect of the embodiment, the formulation to treat sleep disorders may be: 5 mg-9-tetrahydrocannabinol (THC), 5 mg cannabidiol (CBD), and 5 mg cannabigerol (CBG). The combined mixture may be compounded into a liquid form for inhalation using a vaporizer.

In another aspect of the embodiment, the terpene myrcene will be added to the formulation to raise the saturation level of a predominant cannabinoid receptor such as CB1 for cannabinoids such as THC, increase permeability of the cell membrane, and decrease the resistance across the blood-brain barrier for medicinal compounds known to be present in *cannabis* extracts, thus potentiating the effects of these medically effective compounds at several major sites of action.

One or more different formulations may be described in the present application. Further, for one or more of the formulations described herein, numerous alternative embodiments may be described. It should be understood that these are presented for illustrative purposes only; the described embodiments are not intended to be limiting in any sense. In general, embodiments are described in sufficient detail to enable those skilled in the art to practice one or more of the formulations, and it is to be understood that other embodiments may be utilized and that structural, compound constituent, constituent compound ratio, constituent compound isomer, constituent compound concentration and other changes may be made without departing from the scope of the particular formulations. When an active compound with multiple naturally occurring isomers is cited, it is to be understood that a mixture containing concentrations of those isomers as are found in nature in *cannabis* is in use unless otherwise specified. Accordingly, those skilled in the art will recognize that one or more of the formulations may be practiced with various modifications and alterations. Particular features of one or more of the formulations may be described with reference to one or more particular embodiments or figures that form a part of the present disclosure, and in which are shown, by way of illustration, specific embodiments of one or more of the formulations. It should be understood, however, that such features are not limited to usage in the one or more particular embodiments or figures with reference to which they are described. The present disclosure is neither a literal description of all embodiments of one or more of the formulations nor a listing of features of one or more of the formulations that must be present in all embodiments.

Cannabinoids, terpenes and flavonoids employed in aspects are to be assumed isolated and purified by previously published means best suited for that active compound which may include but are not limited to HPLC, also known as high pressure liquid chromatography, distillation, fractional distillation, steam distillation, supercritical fluid extraction, either with or without additional, modifying solvents as well as other methods known to those skilled in the art.

When single cannabinoids, multiple cannabinoid mixtures, cannabinoid-terpene mixtures, cannabinoid-terpene-flavonoid, terpene, multiple terpene and terpene-flavonoid mixtures are listed in embodiments, they are to be assumed administered by methods previously cited to both retain the stability of all active compounds cited in a formulation and to effect delivery of all active compounds within the formulation. These delivery methods may comprise, but are not limited to, administering the orally, anally, or via injection compounds containing a known amount of the formulation, inhalation of vapor comprising the formulation, administration of sublingual tinctures of the formulation, extracts of the formulation, oils of the formulation, capsules of the formulation and tablets of the formulation as well as other administrative methods known to be applicable to those with ordinary skill in the art.

It will be readily apparent that more than one method of administration may be used for delivery of a single formulation cited in an embodiment, and that any method of administration that maintains both constituent active compound stability and high bioavailability of each active compound may be employed for a single cited formulation.

Techniques and mechanisms described or referenced herein will sometimes be described in singular form for clarity. However, it should be noted that particular embodiments include multiple iterations of a technique or multiple manifestations of a mechanism unless noted otherwise.

DETAILED DESCRIPTION OF EXAMPLES

FIG. 1 is a method diagram illustrating a process 100 for preparing *cannabis* medicinal products, according to a preferred aspect. The overall process of creating medicinal products from the *cannabis* plant consists of six stages: cultivation 101, extraction 102, concentration 103, separation 104, secondary concentration 105, and processing 106. At the cultivation stage 101, the *cannabis* plants are grown and harvested. The harvested plant matter, or selected portions of it, is sent for extraction 102, at which point essential oils of the plant are extracted, which contain some plant matter in the form of chlorophyll, plant waxes, plant lipids, plus substantial amounts of cannabinoids, terpenes, and flavonoids. These oils are concentrated 103 via evaporation. In the separation stage 104, the *cannabis* compounds are separated from the concentrated oils via a variety of processing methods, usually involving high pressure liquid chromatography or flash chromatography. At this stage, the purified *cannabis* compounds (cannabinoids, terpenes, and flavonoids) are sent for further concentration 105 via evaporation. Said concentrated, purified *cannabis* compounds are then processed 106 with other ingredients to create medicinal products, for example pills, tablets, salves, injectables, etc.

In an aspect, additional amounts of the terpene myrcene is added to the product in step 106 to take advantage of the unique advantages presented by -myrcene, which is shown to increase the permeability of the cell membrane, decrease the resistance across the blood-brain barrier, and increase saturation at the CB1 receptor site for a plurality of compounds including itself, other terpenes, and cannabinoids including but not limited to THC. For example, infusing myrcene as well as THC into the product in step 106 may ensure that THC's (or, for other therapeutic effects, cannabinoids such as CBD, CBN, or CBG) maximal activation level may be increased by a biologically significant amount, and that increase may be achieved at a faster rate. Formulations including selected THC, other cannabinoids and terpenes in the presence of myrcene may significantly augment the efficacy of such formulations for the desired biological and medicinal effects. One analgesic and anti-inflammatory formulation may be: 0.30% w/w to 50% -myrcene, 20% w/w to 35% w/w cannabidiol (CBD), 10% w/w to 25% w/w -pinene, 5% w/w to 15% w/w terpineol, and 10% w/w to 30% borneol. Another myrcene-enhanced analgesic and anti-inflammatory formulation may be 0.25% w/w to 40% w/w -myrcene, 10% w/w to 20% w/w cannabidiol (CBD), 5% w/w to 15% w/w p-cymene and 15% w/w to 30% borneol.

Figure 2:
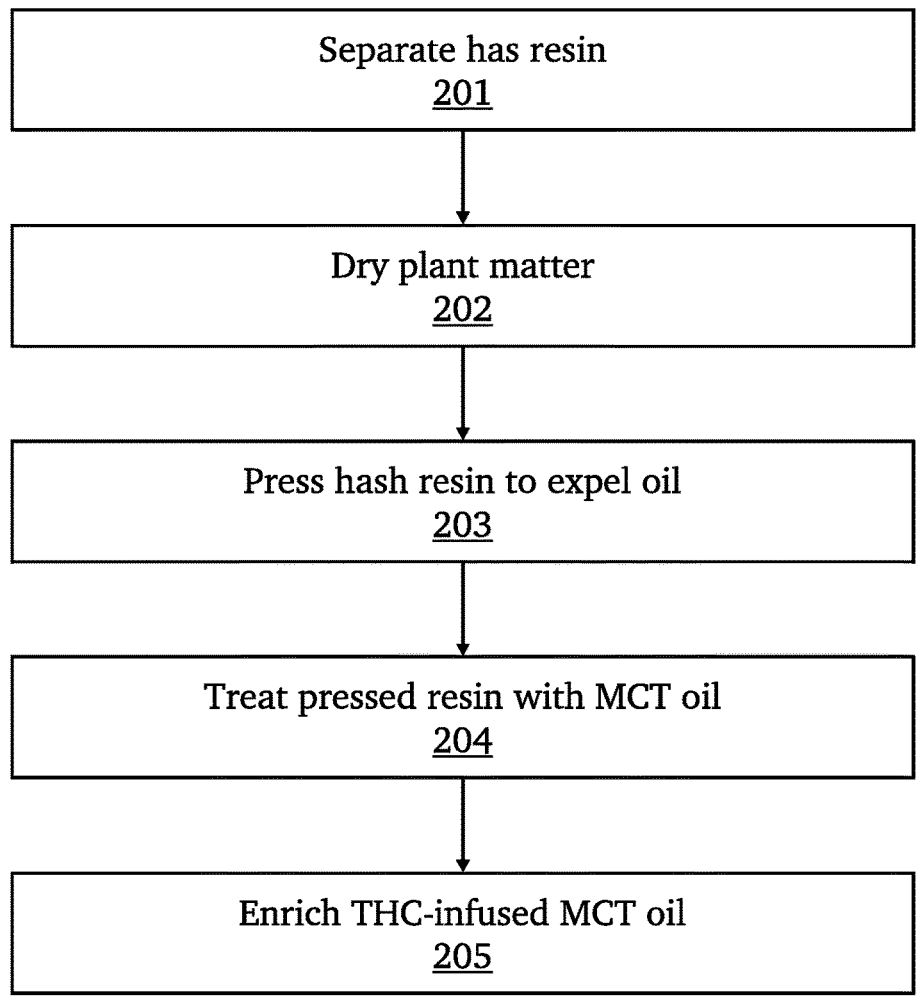
FIG. 2 is a method diagram illustrating a process for preparing an enhanced smokable therapeutic *cannabis* product using hash resin, according to a preferred embodiment.

FIG. 2 is a method diagram illustrating a process 200 for preparing an enhanced smokable therapeutic *cannabis* product using hash resin, according to a preferred embodiment. The inventors have discovered, in particular, that using the methods described herein rather than, as is commonly done in the art, infusing smokable plant material directly with hash resin, provides a superior product that tastes better, smokes more smoothly, and has predictable therapeutic effects (which may in fact be varied, according to aspects of the invention, by varying the cannabinoid profile of the oil used to spray plant matter in step 206, as described below). According to a preferred aspect, dried *cannabis* plant matter is treated to separate hash resin 201, as is known in the art, and the remaining plant matter is further dried until it is substantially moisture-free 202. In another step, the hash resin is pressed to expel oils 203 (which are used for other purposes); it will be appreciated by those having ordinary skill in the art that the resulting oil will be very rich in cannabinoids and terpenes (as well as flavonoids), as described above. Further, the pressed hash resin is treated with an oil rich in medium-chain triglycerides (MCT oil) 204, which extracts a substantial amount of THC and other cannabinoids; this MCT-based, THC-infused oil represents a recovered fraction of the THC present in the hash resin. The THC-infused MCT oil may be further enriched 205 by addition of pure P myrcene and other desired cannabinoids, terpenes, and flavonoids as desired (for different aspects, different cannabinoid profiles may be used to enrich the THC-infused MCT oil, depending on the desired therapeutic effect).

According to a preferred aspect, the terpene myrcene is added to MCT oil 205 to take advantage of the unique advantages presented by (-myrcene, which is shown to increase the permeability of the cell membrane, decrease the resistance across the blood-brain barrier, and increase saturation at the CB1 receptor site for a plurality of compounds including itself, other terpenes, and cannabinoids including but not limited to THC. For example, infusing myrcene as well as THC into the MCT oil prior to spraying dried, smokable *cannabis* plant matter 205 may ensure that THC's (or, for other therapeutic effects, cannabinoids such as CBD, CBN, or CBG) maximal activation level may be increased by a biologically significant amount, and that increase may be achieved at a faster rate. Formulations including selected THC, other cannabinoids and terpenes in the presence of myrcene may significantly augment the efficacy of such formulations for the desired biological and medicinal effects.

A person with ordinary skill in the art will be aware of a range of possible modifications of the various embodiments described above. Accordingly, the present invention is defined by the claims and their equivalents.

What is claimed is:

1. A method of preparing a *cannabis*-based therapeutic product for the treatment of chronic pain, the method comprising the steps of:
    (a) separating hash resin from plant material of a *cannabis* plant of a specific strain;
    (b) pressing the hash resin to expel oil, leaving spent hash resin;
    (c) extracting further cannabinoids from the spent hash resin using MCT oil;
    (d) separating the *cannabis* compounds from the oils using high pressure liquid chromatography or flash chromatography;
    (e) mixing *cannabis* compounds obtained via steps (a)-(d) from one or more strains of *cannabis* to obtain a formulation therapeutically-effective for use in treating chronic pain; and
    (f) processing the formulation from step (e) into a pill or tablet suitable for therapeutic administration to a human patient;
    wherein the formulation comprises at least 5% w/w β-myrcene, between 20% w/w and 35% w/w cannabidiol, at least 10% α-pinene, at least 5% w/w terpineol, and at least 10% w/w borneol.

2. The method of claim 1, wherein the formulation further comprises at least 5% w/w p-cymene.

3. A *cannabis*-based treatment product for chronic pain produced according to the method of claim 1.

4. A *cannabis*-based treatment product for chronic pain produced according to the method of claim 2.

* * * * *